US008539947B2

(12) United States Patent
Kuhn et al.

(10) Patent No.: US 8,539,947 B2
(45) Date of Patent: Sep. 24, 2013

(54) POWDER INHALER

(75) Inventors: Rolf Kuhn, Ingelheim am Rhein (DE); Burkhard Peter Metzger, Ingelheim am Rhein (DE); Torsten Kuehn, Appenheim (DE); Heinrich Kladders, Muelheim-Ruhr (DE); Joern-Eric Schulz, Muenster (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 404 days.

(21) Appl. No.: 12/669,187

(22) PCT Filed: Jul. 17, 2008

(86) PCT No.: PCT/EP2008/059388
§ 371 (c)(1),
(2), (4) Date: Apr. 20, 2010

(87) PCT Pub. No.: WO2009/013218
PCT Pub. Date: Jan. 29, 2009

(65) Prior Publication Data
US 2010/0275917 A1    Nov. 4, 2010

(30) Foreign Application Priority Data

Jul. 20, 2007   (DE) .......................... 10 2007 033 861
Aug. 2, 2007   (DE) .......................... 10 2007 036 411

(51) Int. Cl.
*A61M 16/00*   (2006.01)
(52) U.S. Cl.
CPC ..................................... *A61M 16/00* (2013.01)
USPC ............ 128/203.21; 128/203.15; 128/203.12; 128/200.24

(58) Field of Classification Search
USPC .............. 128/200.24, 203.12, 203.15, 203.21
See application file for complete search history.

(56) References Cited

U.S. PATENT DOCUMENTS 3,403,679 A * 10/1968 Cyril et al. ..................... 604/138
3,918,451 A * 11/1975 Steil .......................... 128/203.21
(Continued)

FOREIGN PATENT DOCUMENTS

CA    2 338 323       2/2000
CA    2510779 A1     7/2004
(Continued)

OTHER PUBLICATIONS

International Search Report for PCT/EP2008/059388 mailed Nov. 6, 2008.

*Primary Examiner* — Annette Dixon
(74) *Attorney, Agent, or Firm* — Michael P. Morris; Wendy A. Petka

(57) ABSTRACT

An inhaler for inhaling powdered medicaments from capsules, having: a lower part which is cup-shaped, a plate latched to the lower part to close off the lower part, a capsule holder arranged on the underside of the plate, a mouthpiece that can be latched to the top of plate, and an actuating member for interacting with at least one pin for piercing a capsule in the capsule holder, where the actuating member includes a larger outer actuating member and a smaller inner actuating member, the outer actuating member forms a user-operated push-button, the inner actuating member contacts and holds the pin below a suspension element of the outer actuating member from the plate, and the point of application of force by the user onto push-button is lower than the inner actuating member.

13 Claims, 1 Drawing Sheet

(56) References Cited

U.S. PATENT DOCUMENTS

| | | | |
|---|---|---|---|
| 5,715,811 A * | 2/1998 | Ohki et al. | 128/203.21 |
| 5,947,118 A | 9/1999 | Hochrainer et al. | |
| 7,252,087 B2 | 8/2007 | Wachtel et al. | |
| 7,878,193 B2 | 2/2011 | Kladders et al. | |
| 8,298,575 B2 | 10/2012 | Hochrainer et al. | |
| 2003/0070679 A1 * | 4/2003 | Hochrainer et al. | 128/203.15 |
| 2004/0152720 A1 | 8/2004 | Hartig et al. | |
| 2005/0279357 A1 | 12/2005 | Wachtel et al. | |
| 2006/0237016 A1 * | 10/2006 | Wachtel | 128/205.21 |
| 2006/0239930 A1 | 10/2006 | Lamche et al. | |
| 2006/0254584 A1 | 11/2006 | Wachtel et al. | |
| 2007/0031347 A1 | 2/2007 | Hartig et al. | |
| 2007/0107722 A1 | 5/2007 | Hoelz et al. | |
| 2007/0295332 A1 * | 12/2007 | Ziegler et al. | 128/203.15 |
| 2008/0160076 A1 | 7/2008 | Hochrainer et al. | |
| 2008/0295832 A1 * | 12/2008 | Geser et al. | 128/203.15 |
| 2011/0036733 A1 | 2/2011 | Balthes et al. | |
| 2011/0232637 A1 * | 9/2011 | Kaemper et al. | 128/203.12 |

FOREIGN PATENT DOCUMENTS

| | | |
|---|---|---|
| CA | 2513201 A1 | 7/2004 |
| EP | 0911047 A1 | 4/1999 |
| EP | 1100474 A2 | 5/2001 |
| JP | 2006516135 A | 6/2006 |
| WO | WO-97 02061 | 1/1997 |
| WO | WO-00 07572 | 2/2000 |
| WO | 02098874 A2 | 12/2002 |
| WO | 2004062640 A2 | 7/2004 |

* cited by examiner

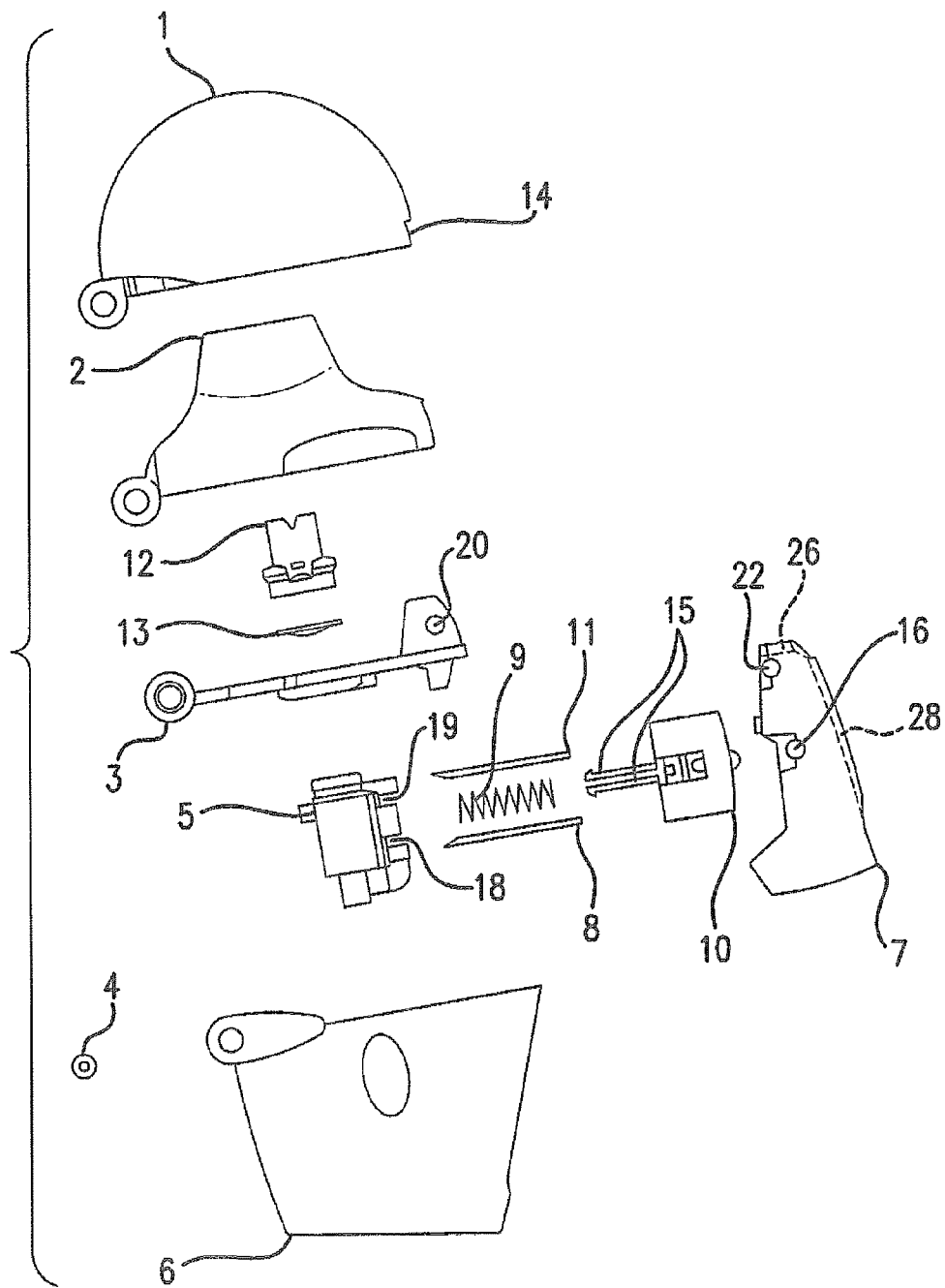

POWDER INHALER

This application is the national phase entry under 35 U.S.C. §371 of International Application No. PCT/EP2008/059388, filed Jul. 17, 2008, which claims priority to German Patent Application No. 102007033861.0, filed Jul. 20, 2007 and German Patent Application No. 102007036411.5, filed Aug. 2, 2007, each of which is hereby incorporated by reference in its entirety.

BACKGROUND

The invention relates to an inhaler with improved operability for inhaling powdered medicaments from capsules that are inserted in a capsule holder arranged in the inhaler prior to use. After the capsules have been placed in the capsule holder, the patient can press an actuating member, which can be set in motion from a resting position and thereby interacts with at least one pin adapted to be pushed into the capsule holder. Using the minimum of one pin the capsule is pierced and the medicament is released.

An inhaler of this kind is described for example in EP 0 703 800 B1 or EP 0 911 047 A1. The inhaler known from the above mentioned specifications has a dish-shaped lower part and an equally dish-shaped cover which fits it, these two parts being capable of being flipped apart for use, about a joint provided in the edge portion. Between the lower part and the cover, a mouthpiece which can also be flipped open and a plate below it with a capsule holder provided underneath also act on the joint. After the individual assemblies have been flipped open the patient can insert a drug-filled capsule in the capsule holder, pivot the plate and capsule holder and the mouthpiece into the lower part and pierce the capsule by means of a spring loaded actuating member projecting laterally from the lower part. The patient being treated then draws the pharmaceutical composition into his airway by sucking on the mouthpiece.

SUMMARY OF THE INVENTION

The intention is to improve the known inhalers still further in terms of their handling.

This aim is achieved according to the invention with an inhaler in which the actuating member is enlarged and is constructed such that the pin holder is situated above the point of application of the force and below the suspension of the push-button.

This results in a genuine reduction in the force required by the user to press the pin or pins through the capsule wall In addition there is a subjective reduction in force for the user on account of the enlarged surface of the push-button compared with the devices known from the prior art. For an inhaler known from the prior art the user has to apply about 35 Newtons in order to pierce the capsule with the pin or pins using the actuating member. In the inhaler according to the invention, 10-25 Newtons, preferably 15-20 Newtons are required.

The cover has an inwardly or outwardly extending bead, which is not externally visible. This bead serves to close the cover at the button, which is located on the lower part of the inhaler.

To enable the cover to be removed from the lower part the actuating member comprises on its upper side a recess which is inclined so as to form a sliding surface for the closure element in the form of a sloping plane and to release the cover from the lower part on actuation and hence when the actuating member is advanced. The recess in the actuating member may vary in size. The minimum size must be sufficient to enable the cover to be released from the lower part in the manner of a pocket watch. The maximum size depends on the top of the actuating member. The actual opening movement of the cover can then be carried out as before, by the patient grasping the cover and flipping it fully open.

The mouthpiece that can be flipped away may be provided with one or two gripping aids that ensure quick and reliable opening of the mouthpiece. Each gripping aid may be arranged so that the contact with the mouthpiece is outside the area that the patient requiring treatment has to place in his mouth for suction. The contact surface for opening and the contact surface for suction are clearly separated from one another by the shape and design of the mouthpiece. Preferably, the gripping aids are located to the left and right of the button and the two gripping aids do not converge in the region of the button. This gives the mouthpiece an optically and practically improved appearance that allows intuitive handling for the user and at the same time provided optimum hygiene conditions. This is particularly important in the area around the mouthpiece, as this component is placed in the oral cavity when the inhaler is used.

In one embodiment, to assist the opening movement, at least one other spring element may be disposed between the plate and lower part, which are of suitable dimensions to allow the cover and/or mouthpiece to snap open. Alternatively, an embodiment without a spring element is also possible.

The actuating member is of particular importance at the start of an asthma attack. Thanks to the effective arrangement of the actuating member combined with the reduced force required from the patient the inhaler is significantly easier to operate. This is particularly valuable when patients are suffering from arthritis or similar diseases or have restricted movement in their fingers for other reasons.

The actuating member consists of a two-part construction, having an inner part and an outer part that are snap-fitted to one another. The inner part has two parallel guide arms (see below). When the actuating member is actuated, the outer part presses with a part of a circle on the inner part, which then moves in a linear manner to push the pins into the capsule.

The actuating member is attached to the plate that can be latched to the lower part. This can be done, for example, by means of snap-fit hooks, latching hooks or similar technical means.

Preferably the actuating member is displaceably mounted on the plate or capsule holder. The plate and/or the capsule holder thus form(s) an abutment for the multi-functional actuating member, which slides along the plate as it moves from the resting position into the desired functional position and is thereby guided by means of a guide rail, for example.

In a favourable embodiment the actuating member is spring-loaded. The restoring force which is already present in the resting position ensures that after the inhaler has been used the actuating member is returned to the resting position and thus the inhalation process can be started or continued.

Advantageously the actuating member comprises a main body and two parallel guide arms engaging thereon. The guide arms project into the lower part and by means of corresponding built-in parts, for example with guide sleeves arranged on the outside of the capsule holder, serve to guide the actuating member during the movement from the resting position into the respective functional positions and back into the resting position.

The guide arms may comprise end stops at their end remote from the main body, which abut on the guide sleeves in the resting position. In this way the actuating member is put under tension.

The guide arms may be of any desired shape and arrangement (e.g. convergent or divergent). In addition, more than two guide arms may be provided.

In all, the actuating member has two abutment regions; one is for the inside of the button and the other is for the outside of the button.

In a preferred embodiment the main body of the actuating member may have a grooved surface. This grooved surface may be on the top or at the side. Preferably, the grooved surface will be in a gripping depression provided in the actuating member.

The gripping surface acts both as a design element and as a means to provide optimum grip during actuation. It is located on the main body of the actuating member outside the inhaler region and therefore does not come into contact with the patient's mouth. In addition, the grooved surfaces may be smaller in area than the overall surface of the actuating member while still guaranteeing safe and rapid use of the inhaler.

Advantageously the upper grooved surface in the resting position has a recess in its region close to the cover for accommodating the closure element of the cover. Within the recess the side wall directed towards the lateral grooved surface is inclined so that as the main body is pushed in, this side wall forms a sliding surface for the closure element and in this way the closure element together with the cover is lifted out of the latched position.

Advantageously the plate latched to the lower part can be detached from the lower part so that the plate can be pivoted away from the lower part. This pivot function makes cleaning of the inhaler easier. The engagement between plate and lower part can be achieved using the retaining flaps mentioned earlier.

It is also possible to construct the inhaler according to all the embodiments so that the actuating member having the minimum of one pin which can penetrate into the capsule holder is attached to the plate such that it can be released from the lower part and swivelled away together with the plate latched to the lower part. Preferably, the actuating member is attached to the plate so that the two parts together form a pivotable unit.

BRIEF DESCRIPTION OF THE DRAWING

To assist in the understanding of the invention it will now be described more fully by reference to the FIGURE (FIG. 1) that follows, wherein:

FIG. 1: is an exploded view with actuating member and mouthpiece with gripping aid

DETAILED DESCRIPTION OF THE INVENTION

FIG. 1 shows the inhaler in an exploded view. The essential assemblies are the lower part 6 which accommodates the plate 3 and is covered by the latter, the mouthpiece 2 which can be latched to the lower part 6 via the retaining lugs of the screen housing 12 and the cover 1 which is formed to complement the lower part 6.

In the closed position of the inhaler the closure element 14 on the cover 1 engages on the plate 3 and is held there by frictional engagement. It is also possible to obtain interlocking engagement by the provision of bead-like structures on the closure element 14. For the closure element 14 on the cover 1 to engage on the plate 3, the outer actuating member 7 comprises a recess 26 into which the closure element 14 is lowered during the closing operation. The recess 26 is provided with an inclined side wall and is located in the area nearest the cover.

The actuating member consists of an outer actuating member 7, suspended from plate 3 by suspension means 20 and 22 together, and an inner actuating member 10. The outer actuating member 7 has a lateral grooved surface 28 on its outer surface which remains outside the inhaler. In order to open the cover 1 first of all the outer actuating member 7 is moved or pressed in the direction of the inhaler. The closure element 14 on the cover 1 impacts the inclined side wall of the recess, which, as the closure element 14 continues to advance, acts as a sliding surface and ensures release of the cover 1.

The recess 16 connects the outer and inner actuating members 7 and 10 by means of a suspension in the form of a snap-fit hook, pin or other suspension means, for example. The recess 16 may be round or oval in shape. The oval may be arranged in a horizontal or vertical position or in any position.

Preferably, the recess 16 is a so-called oblong hole, i.e. an elongate hole or oval which allows optimum guidance of the pins 8 and 11 in the axial direction, so as to ensure precise piercing of the capsule.

The lower part 6 is cup-shaped and accommodates the whole of the capsule holder 5 arranged on the underside of the plate 3. However, in order to insert a capsule filled with medicament (not shown) in the capsule holder 5, the mouthpiece 2 must also be flipped out of the way. In the embodiment according to FIG. 1 this is done by acting on the outer actuating member 7. In this opened position of the cover 1 and mouthpiece 2 the capsule can be placed in the capsule holder 5 through an opening in the plate 3. Then the mouthpiece 2 is swivelled back again and closed again by latching the retaining lugs of the screen housing 12 in the plate 3. The screen housing 12 contains the screening mesh 13 in its centre. The screening mesh 13 is made of standard commercial materials such as metal or plastics, for example. In the latter case, the screen may be made by injection moulding. For releasing the active substance the outer actuating member 7 is actuated. Its construction is such that the inner actuating member 10 contacts the pin or pins and is located above the point of application of the force and below the point of suspension of the push-button. On the inner actuating member 10 there is at least one pin, but preferably two perpendicularly offset, parallel pins 8, 11, moving continuously as the actuating member 7, 10 is pushed in towards the capsule (not shown) and perforating it. The perforation process can be observed through an inspection window (not shown).

In the capsule holder 5 there is one or at least two tubular pin passages 18 and 19 which are aligned axially in accordance with the direction of movement of the pin or pins 8, 11. On the one hand these ensure that the pin or pins 8, 11 are correctly aimed at the capsule (not shown) and on the other hand they provide additional guidance of the actuating member 7, 10. However, the essential guiding is done by two guide arms 15 arranged laterally. The guide arms 15 also have the task of holding the actuating member 7, 10 under spring bias. For this purpose the guide arms 15 are provided at their end remote from the main body with end stops which abut on the guide sleeves of the capsule holder 5 in the resting position of the actuating member 7, 10. The guide sleeves are located on the outside of the capsule holder 5. Between the guide arms 15 is arranged a helical spring 9 which extends parallel to the pin or pins 8, 11 in its axial direction, the helical spring 9 being matched to the length of the guide arms 15 such that the actuating member 7, 10 is under tension even in the resting position.

The individual assemblies made up of the lower part 6, plate 3, mouthpiece 2 and cover 1 are connected by means of hinge recesses and a spindle 4 and are all movable or pivotable relative to one another about this spindle.

The pins used may be any pins known to the skilled man. They may be solid or hollow pins. Preferably, solid pins are used. In particular, the upper pin (facing the mouthpiece) may be a triangular pin with a triangular point. The lower pin may be a standard pin with a standard point, as laid down in the German DIN standard, for example.

Alternatively the upper pin may be a standard pin with a standard point and the lower pin may be a triangular pin with a triangular point.

As a second alternative it is possible to use two triangular pins with triangular points or two standard pins with standard points.

The capsules used may be any of the capsules known in the art for powder inhalers (such as (hard) gelatine, plastic or metal capsules). A plastic capsule, in particular, may be used in the inhaler according to the invention, as disclosed in WO 00/07572, EP 1 100 474.

The inhaler may have an inspection window. However, this is not essential for it to function in the intended manner.

Similarly, all the components of the inhaler may be modified by methods known to the skilled man and according to the possibilities availability in plastics technology. Possible modifications include, for example, reinforcing or altering the wall thickness. However, these possibilities are not absolutely essential to the operation of the inhaler.

The inhaler may also be coated on its inside or outside by methods known in the art.

It may be used for the inhalation of all kinds of powdered medicaments which it is therapeutically advisable to administer by inhalation.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

- W denotes a betamimetic, combined with an anticholinergic, corticosteroid, PDE4-inhibitor, EGFR-inhibitor or LTD4-antagonist,
- W denotes an anticholinergic, combined with a betamimetic, corticosteroid, PDE4-inhibitor, EGFR-inhibitor or LTD4-antagonist,
- W denotes a corticosteroid, combined with a PDE4-inhibitor, EGFR-inhibitor or LTD4-antagonist
- W denotes a PDE4-inhibitor, combined with an EGFR-inhibitor or LTD4-antagonist
- W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5.6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2.4.6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1-dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2.6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

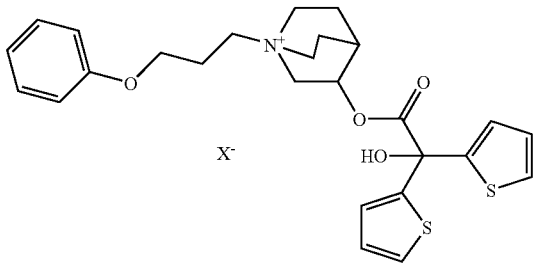

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

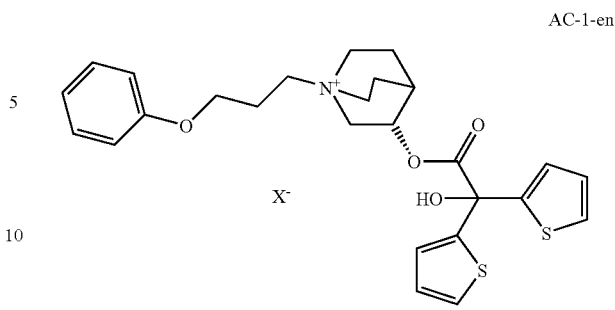

AC-1-en wherein X⁻ may have the above-mentioned meanings. Other preferred anticholinergics are selected from the salts of formula AC-2

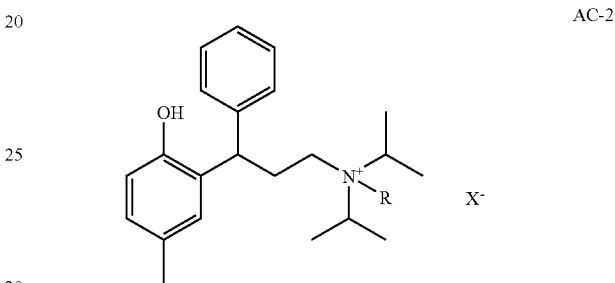

AC-2 wherein R denotes either methyl or ethyl and wherein X⁻ may have the above-mentioned meanings. In an alternative embodiment the compound of formula AC-2 may also be present in the form of the free base AC-2-base.

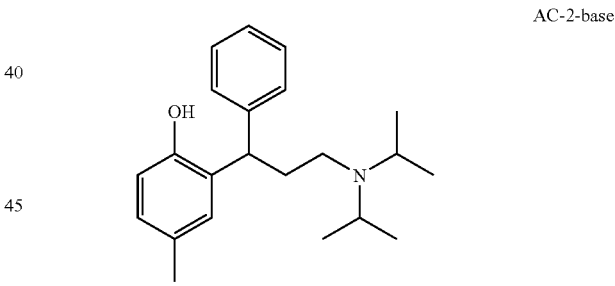

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;

cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for $X^-$.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl) 6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17 α-(2,2,3,3-tetramethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4.3-a]pyridine
9-cyclopentyl-5,6-dihydro-7-ethyl-3-(tert-butyl)-9H-pyrazolo[3,4-c]-1,2,4-triazolo[4.3-a]pyridine
optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-(((R)-(3-(2-(6,7-difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and
4-[(3-chloro-4-fluorophenyl)amino]-6-{[4-(morpholin-4-yl)-1-oxo-2-buten-1-yl]-amino-}-7-cyclopropylmethoxy-quinazoline
4-[(3-chloro-4-fluorophenyl)amino]-6-{[4-(N,N-diethylamino)-1-oxo-2-buten-1-yl]-amino-}-7-cyclopropylmethoxy-quinazoline
4-[(3-chloro-4-fluorophenyl)amino]-6-{[4-(N,N-dimethylamino)-1-oxo-2-buten-1-yl]amino}-7-cyclopropylmethoxy-quinazoline
4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2.2-dimethyl-6-oxo-morpholin-4-yl)-ethoxy]-7-methoxy-quinazoline 4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2.2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2.2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The pharmaceutically active substances, substance formulations or substance mixtures used may be any inhalable compounds, including, for example, inhalable macromolecules, as disclosed in EP 1 003 478. Preferably, substances, substance formulations or substance mixtures that are used by inhalation may be used to treat respiratory complaints.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

LIST OF REFERENCE NUMERALS 1 cover
2 mouthpiece
3 plate
4 spindle
5 capsule holder
6 lower part
7 outer actuating member
8 pin
9 helical spring
10 inner actuating member
11 pin
12 screen housing
13 screening mesh
14 closure element
15 guide arms(s)
16 recess

The invention claimed is:

1. An inhaler for inhaling powdered medicaments from capsules, comprising
   a lower part (6) which is cup-shaped,
   a plate (3) latched to the lower part (6), by means of which the lower part (6) can be closed off, and a capsule holder (5) that is arranged on the underside of the plate (3), wherein the lower part (6) accommodates the whole of the capsule holder (5),
   a mouthpiece (2) that can be latched to the top of plate (3), and
   an actuating member which can be set in motion from a resting position and interacts with at least one pin (8, 11), that can be pushed into the capsule holder (5) in order to pierce a capsule in the capsule holder,
wherein the actuating member is in two parts of an outer actuating member (7) and an inner actuating member (10) and wherein
   the outer actuating member (7) is larger than the inner actuating member (10),
   the outer actuating member (7) forms a push-button that is operated by the patient and is moveably suspended from the plate (3) by means for suspension (20, 22),
   the inner actuating member (10) contacts and holds the at least one pin and is situated below the means for suspension (20, 22) of the outer actuating member (7) from the plate (3), and
   the point of application of force by the user onto the outer actuating member push-button is lower than the inner actuating member (10).

2. The inhaler according to claim 1, wherein 10-25 Newtons have to be applied in order to perforate the capsule by pushing the outer actuating member (7).

3. The inhaler according to claim 1, wherein the actuating member (7, 10) is spring-loaded so that after actuation the actuating member (7, 10) is returned to its rest position.

4. The inhaler according to claim 1, wherein the inner actuating member (10) is attached to the outer actuating member (7) and the inner actuating member contains guide arms (15) for guiding the at least one pin (8, 11) into the capsule holder.

5. The inhaler according to claim 1, wherein the outer actuating member (7) is grooved and comprises at least one lateral grooved surface (28).

6. The inhaler according to claim 1, wherein the inhaler has a cover (1) which covers the mouthpiece (2) in a closure position and latches by means of a closure element (14) and that the outer actuating member (7) has, on its upper side, a recess (26) which is inclined so as to form a sliding surface for the closure element (14) in the form of a sloping plane.

7. The inhaler according to claim 1, wherein the piercing of the a capsule is carried out by two or more perpendicularly offset, parallel pins (8, 11) that are moved by the actuation of the outer actuating member (7) which moves the inner actuating member (10) which contacts the pins and pushes them into the capsule holder (5) to perforate the capsule.

8. The inhaler according to claim 7, wherein the inhaler has two or more tubular pin passages (18, 19) provided in the capsule holder (5) and that upon actuation the pins (8, 11) are passed through these tubular pin passages.

9. The inhaler according to claim 4, wherein the guide arms (15) are provided with end stops at their end remote from the main body, wherein the end stops abut on the capsule holder (5) in the resting position of the actuating member (7, 10).

10. The inhaler according to claim 1, which further contains a plastic capsule containing a powdered medicament in the capsule holder (5).

11. The inhaler according to claim 1, wherein, upon actuating by pushing on the outer actuating member (7), the outer actuating member (7) moves along a part of a circle around the means for suspension (20, 22) and presses onto the inner actuating member (10) such that the inner actuating member (10) moves in a linear manner and pushes the pins into the capsule holder.

12. The inhaler according to claim 11, wherein the inner actuating member (10) is attached to the outer actuating member (7) by a suspension means attaching at recess (16) which is in the form of an elongate hole, such that the attachment allows the inner actuating member (10) to move in a linear manner as a result of the outer actuating member (7) moving along a part of a circle around the means for suspension (20, 22).

13. The inhaler according to claim 1, wherein the inner actuating member (10) is attached to the capsule holder (5).

* * * * *